(12) United States Patent
Zhou et al.

(10) Patent No.: US 9,024,086 B2
(45) Date of Patent: *May 5, 2015

(54) HYDROGENATION CATALYSTS WITH ACIDIC SITES

(71) Applicant: Celanese International Corporation, Irving, TX (US)

(72) Inventors: Zhenhua Zhou, Houston, TX (US); Heiko Weiner, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 113 days.

This patent is subject to a terminal disclaimer.

(21) Appl. No.: 13/734,559

(22) Filed: Jan. 4, 2013

(65) Prior Publication Data

US 2013/0184501 A1    Jul. 18, 2013

Related U.S. Application Data

(63) Continuation-in-part of application No. 13/595,365, filed on Aug. 27, 2012, now Pat. No. 8,865,609, which is a continuation-in-part of application No. 13/595,358, filed on Aug. 27, 2012, which is a continuation-in-part of application No. 13/595,340, filed on Aug. 27, 2012.

(60) Provisional application No. 61/583,874, filed on Jan. 6, 2012, provisional application No. 61/583,922, filed on Jan. 6, 2012.

(51) Int. Cl.
| | |
|---|---|
| C07C 27/04 | (2006.01) |
| B01J 23/89 | (2006.01) |
| B01J 23/652 | (2006.01) |
| B01J 23/62 | (2006.01) |
| C07C 29/149 | (2006.01) |
| B01J 37/02 | (2006.01) |
| B01J 37/08 | (2006.01) |
| B01J 23/00 | (2006.01) |
| B01J 23/96 | (2006.01) |
| B01J 23/94 | (2006.01) |
| B01J 23/888 | (2006.01) |
| B01J 35/00 | (2006.01) |
| B01J 23/06 | (2006.01) |
| B01J 23/10 | (2006.01) |
| B01J 23/14 | (2006.01) |
| B01J 23/20 | (2006.01) |
| B01J 23/24 | (2006.01) |
| B01J 23/34 | (2006.01) |
| B01J 23/38 | (2006.01) |
| B01J 23/70 | (2006.01) |
| B01J 21/12 | (2006.01) |

(52) U.S. Cl.
CPC .......... B01J 23/8993 (2013.01); B01J 23/6527 (2013.01); B01J 23/626 (2013.01); C07C 29/149 (2013.01); B01J 37/0244 (2013.01); B01J 37/08 (2013.01); B01J 37/0205 (2013.01); B01J 23/002 (2013.01); B01J 23/06 (2013.01); B01J 23/10 (2013.01); B01J 23/14 (2013.01); B01J 23/20 (2013.01); B01J 23/24 (2013.01); B01J 23/34 (2013.01); B01J 23/38 (2013.01); B01J 23/70 (2013.01); B01J 23/898 (2013.01); B01J 23/8986 (2013.01); B01J 23/96 (2013.01); B01J 2523/00 (2013.01); B01J 23/94 (2013.01); B01J 21/12 (2013.01); B01J 23/888 (2013.01); B01J 35/002 (2013.01)

(58) Field of Classification Search
CPC ...................................... C07C 29/153
USPC .......................... 568/885; 501/100
See application file for complete search history.

(56) References Cited

U.S. PATENT DOCUMENTS

| | | |
|---|---|---|
| 1,469,447 A | 10/1923 | Schneible |
| 2,591,671 A | 4/1952 | Catterall |
| 2,591,672 A | 4/1952 | Catterall |
| 2,607,719 A | 8/1952 | Eliot et al. |
| 2,702,783 A | 2/1955 | Harrison et al. |
| 2,715,604 A | 8/1955 | Weaver, Jr. |
| 2,744,939 A | 5/1956 | Kennel |
| 2,801,209 A | 7/1957 | Muller et al. |
| 3,102,150 A | 8/1963 | Hunter et al. |
| 3,361,769 A | 1/1968 | Halpern et al. |
| 3,404,186 A | 10/1968 | Bailey et al. |
| 3,408,267 A | 10/1968 | Miller et al. |
| 3,445,345 A | 5/1969 | Katzen et al. |
| 3,531,543 A | 9/1970 | Clippinger et al. |
| 3,864,284 A | 2/1975 | Clippinger et al. |
| 3,953,524 A | 4/1976 | Steiner |
| 3,981,923 A | 9/1976 | Stouthamer et al. |
| 3,990,952 A | 11/1976 | Katzen et al. |
| 4,048,096 A | 9/1977 | Bissot |

(Continued)

FOREIGN PATENT DOCUMENTS

| | | |
|---|---|---|
| CN | 201768393 | 3/2011 |
| CN | 102091429 | 6/2011 |

(Continued)

OTHER PUBLICATIONS

Rachmady, Acetic Acid Reduction by H2 on Bimetallic Pt—Fe Catalysts, Journal of Catalysis 209, 87-98 (Apr. 1, 2002), Elsevier Science (USA).

(Continued)

*Primary Examiner* — Sudhakar Katakam
*Assistant Examiner* — Kofi Adzamli

(57) ABSTRACT

The present invention relates to catalysts and to chemical processes employing such catalysts. The catalysts are preferably used for converting acetic acid to ethanol. The catalyst comprises acidic sites and two or more metals. The catalyst has acidic sites on the surface and the balance favors Lewis acid sites.

19 Claims, 4 Drawing Sheets

(56) References Cited

U.S. PATENT DOCUMENTS

| | | | |
|---|---|---|---|
| 4,199,438 A | 4/1980 | Antos | |
| 4,306,942 A | 12/1981 | Brush et al. | |
| 4,374,265 A | 2/1983 | Larkins, Jr. | |
| 4,395,576 A | 7/1983 | Kwantes et al. | |
| 4,398,039 A * | 8/1983 | Pesa et al. | 560/265 |
| 4,422,903 A | 12/1983 | Messick et al. | |
| 4,448,644 A | 5/1984 | Foster et al. | |
| 4,454,358 A | 6/1984 | Kummer et al. | |
| 4,456,775 A | 6/1984 | Travers et al. | |
| 4,476,326 A | 10/1984 | Lin et al. | |
| 4,514,515 A | 4/1985 | Travers et al. | |
| 4,517,391 A | 5/1985 | Schuster et al. | |
| 4,541,897 A | 9/1985 | Sommer et al. | |
| 4,550,185 A | 10/1985 | Mabry et al. | |
| 4,600,571 A | 7/1986 | McCarroll et al. | |
| 4,628,130 A | 12/1986 | Bournonville et al. | |
| 4,678,543 A | 7/1987 | Houben et al. | |
| 4,760,171 A | 7/1988 | Isogai et al. | |
| 4,761,505 A | 8/1988 | Diana et al. | |
| 4,774,365 A | 9/1988 | Chen et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,837,368 A | 6/1989 | Gustafson et al. | |
| 4,842,693 A | 6/1989 | Wheldon | |
| 4,880,937 A | 11/1989 | Matsushita et al. | |
| 4,943,354 A | 7/1990 | Osterburg et al. | |
| 4,985,572 A | 1/1991 | Kitson et al. | |
| 4,990,655 A | 2/1991 | Kitson et al. | |
| 5,035,776 A | 7/1991 | Knapp | |
| 5,061,671 A | 10/1991 | Kitson et al. | |
| 5,124,004 A | 6/1992 | Grethlein et al. | |
| 5,137,861 A | 8/1992 | Shih et al. | |
| 5,149,680 A * | 9/1992 | Kitson et al. | 502/185 |
| 5,185,476 A | 2/1993 | Gustafson | |
| 5,185,481 A | 2/1993 | Muto et al. | |
| 5,215,902 A | 6/1993 | Tedder | |
| 5,250,271 A | 10/1993 | Horizoe et al. | |
| 5,284,983 A | 2/1994 | Muto et al. | |
| 5,292,704 A | 3/1994 | Lester | |
| 5,292,916 A | 3/1994 | Matsuzaki et al. | |
| 5,350,504 A | 9/1994 | Dessau | |
| 5,391,291 A | 2/1995 | Winquist et al. | |
| 5,405,996 A | 4/1995 | Suzuki et al. | |
| 5,426,246 A | 6/1995 | Nagahara et al. | |
| 5,449,440 A | 9/1995 | Rescalli et al. | |
| 5,476,827 A | 12/1995 | Ferrero et al. | |
| 5,488,185 A | 1/1996 | Ramachandran et al. | |
| 5,585,523 A | 12/1996 | Weiguny et al. | |
| 5,719,097 A | 2/1998 | Chang et al. | |
| 5,767,307 A | 6/1998 | Ramprasad et al. | |
| 5,849,657 A | 12/1998 | Rotgerink et al. | |
| 5,945,570 A | 8/1999 | Arhancet et al. | |
| 5,955,397 A | 9/1999 | Didillon et al. | |
| 5,977,010 A | 11/1999 | Roberts et al. | |
| 6,121,498 A | 9/2000 | Tustin et al. | |
| 6,204,417 B1 | 3/2001 | Fiscer et al. | |
| 6,294,703 B1 | 9/2001 | Hara et al. | |
| 6,414,209 B1 | 7/2002 | Herskowitz et al. | |
| 6,462,231 B1 | 10/2002 | Yanagawa et al. | |
| 6,462,244 B1 | 10/2002 | Huang et al. | |
| 6,495,730 B1 | 12/2002 | Konishi et al. | |
| 6,559,333 B1 | 5/2003 | Brunelle et al. | |
| 6,632,330 B1 | 10/2003 | Colley et al. | |
| 6,670,490 B1 | 12/2003 | Campos et al. | |
| 6,809,217 B1 | 10/2004 | Colley et al. | |
| 6,903,045 B2 | 6/2005 | Zoeller et al. | |
| 6,906,228 B2 | 6/2005 | Fischer et al. | |
| 7,361,794 B2 | 4/2008 | Grosso | |
| 7,375,049 B2 | 5/2008 | Hayes et al. | |
| 7,425,657 B1 | 9/2008 | Elliott et al. | |
| 7,538,060 B2 | 5/2009 | Barnicki et al. | |
| 7,553,397 B1 | 6/2009 | Colley et al. | |
| 7,572,353 B1 | 8/2009 | Vander et al. | |
| 7,594,981 B2 | 9/2009 | Ikeda | |
| 7,608,744 B1 | 10/2009 | Johnston et al. | |
| 7,732,173 B2 | 6/2010 | Mairal et al. | |
| 7,744,727 B2 | 6/2010 | Blum et al. | |
| 7,842,844 B2 | 11/2010 | Atkins | |
| 7,847,134 B2 | 12/2010 | Lee et al. | |
| 7,923,405 B2 | 4/2011 | Kharas et al. | |
| 7,947,746 B2 | 5/2011 | Daniel et al. | |
| 8,002,953 B2 | 8/2011 | Lee et al. | |
| 8,053,610 B2 | 11/2011 | Kikuchi et al. | |
| 8,080,694 B2 | 12/2011 | Weiner et al. | |
| 8,088,832 B2 | 1/2012 | Melnichuk et al. | |
| 8,129,436 B2 | 3/2012 | Tirtowidjojo et al. | |
| 8,173,324 B2 | 5/2012 | Fisher et al. | |
| 8,198,057 B2 | 6/2012 | Padgett | |
| 8,288,596 B2 | 10/2012 | Garton et al. | |
| 8,299,132 B2 | 10/2012 | Gracey et al. | |
| 8,299,133 B2 | 10/2012 | Gracey et al. | |
| 8,309,782 B2 | 11/2012 | Le Peltier et al. | |
| 8,329,961 B2 | 12/2012 | Danjo et al. | |
| 2003/0105171 A1 | 6/2003 | Subramanian et al. | |
| 2006/0102520 A1 | 5/2006 | Lapinski et al. | |
| 2006/0241325 A1 | 10/2006 | Komplin et al. | |
| 2007/0144886 A1 | 6/2007 | Sylvester et al. | |
| 2007/0238605 A1 | 10/2007 | Strehlau et al. | |
| 2008/0135396 A1 | 6/2008 | Blum | |
| 2008/0227627 A1 | 9/2008 | Strehlau et al. | |
| 2009/0088317 A1 | 4/2009 | Frye, Jr. et al. | |
| 2009/0166172 A1 | 7/2009 | Casey | |
| 2010/0029996 A1 | 2/2010 | Danjo et al. | |
| 2010/0121114 A1 | 5/2010 | Johnston et al. | |
| 2010/0197486 A1 | 8/2010 | Johnston et al. | |
| 2010/0197959 A1 | 8/2010 | Johnston et al. | |
| 2010/0249479 A1 | 9/2010 | Berg-Slot et al. | |
| 2011/0004034 A1 | 1/2011 | Daniel et al. | |
| 2011/0046421 A1 | 2/2011 | Daniel et al. | |
| 2011/0060169 A1 | 3/2011 | Kaizik et al. | |
| 2011/0082322 A1 | 4/2011 | Jevtic et al. | |
| 2011/0098501 A1 | 4/2011 | Johnston et al. | |
| 2011/0190117 A1 | 8/2011 | Weiner et al. | |
| 2011/0224462 A1 | 9/2011 | Ditzel et al. | |
| 2012/0209034 A1 | 8/2012 | Zhou et al. | |
| 2012/0238785 A1 | 9/2012 | Zhou et al. | |
| 2013/0184501 A1 | 7/2013 | Zhou et al. | |

FOREIGN PATENT DOCUMENTS

| | | |
|---|---|---|
| CN | 102228831 | 11/2011 |
| CN | 102229520 | 11/2011 |
| CN | 101525272 | 5/2012 |
| DE | 2723611 | 11/1978 |
| EP | 0104197 | 4/1984 |
| EP | 0137749 | 4/1985 |
| EP | 0175558 | 3/1986 |
| EP | 0400904 | 5/1990 |
| EP | 0372847 | 6/1990 |
| EP | 372847 A2 * | 6/1990 |
| EP | 0408528 | 7/1990 |
| EP | 0653242 | 5/1995 |
| EP | 1074299 | 2/2001 |
| EP | 2060553 | 5/2009 |
| FR | 2524339 | 10/1983 |
| JP | 6-116182 | 4/1994 |
| JP | 10-306047 | 11/1998 |
| JP | 11-147845 | 6/1999 |
| JP | 2001-046874 | 2/2001 |
| JP | 2001-157841 | 6/2001 |
| JP | 2009-263356 | 11/2009 |
| JP | 2010-159212 | 7/2010 |
| WO | WO 2007/107371 | 9/2007 |
| WO | WO 2008/135192 | 11/2008 |
| WO | WO 2009/009320 | 1/2009 |
| WO | WO 2009/009322 | 1/2009 |
| WO | WO 2011/053367 | 5/2011 |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

(56) References Cited

OTHER PUBLICATIONS

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

International Search Report and Written Opinion mailed on Apr. 29, 2013 in corresponding International Application No. PCT/US2013/020327.

Office Action for U.S. Appl. No. 13/734,570 dated Dec. 2, 2014.

International Search Report and Written Opinion for PCT/US2013/020327 mailed Apr. 29, 2013.

\* cited by examiner

HYDROGENATION CATALYSTS WITH ACIDIC SITES

CROSS REFERENCE TO RELATED APPLICATION

This application is a continuation-in-part of U.S. application Ser. No. 13/595,365, filed on Aug. 27, 2012, which claims priority to U.S. Provisional App. No. 61/583,874, filed on Jan. 6, 2012. This application is also a continuation-in-part to U.S. application Ser. No. 13/595,358, filed on Aug. 27, 2012, which claims priority to U.S. Provisional App. No. 61/583,922, filed on Jan. 6, 2012. This application is also a continuation-in-part of U.S. application Ser. No. 13/595,340, filed on Aug. 27, 2012, which also claims priority to U.S. Provisional App. No. 61/583,874, filed on Jan. 6, 2012. The entire contents and disclosures of the above applications are hereby incorporated by reference.

FIELD OF THE INVENTION

The present invention relates to hydrogenation catalysts having acidic sites, and to processes for producing ethanol from a feedstock comprising a carboxylic acid and/or esters thereof in the presence of the inventive catalysts. In particular, the present invention relates to hydrogenation catalyst having acidic sites, wherein at least 70% of the acidic sites are Lewis acid sites, as measured by Fourier transform infrared spectroscopy of chemisorbed pyridine (FTIR).

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis,* 2001, 370-379.

U.S. Pat. No. 8,080,694 describes a process for hydrogenating alkanoic acids comprising passing a gaseous stream comprising hydrogen and an alkanoic acid in the vapor phase over a hydrogenation catalyst comprising: a platinum group metal selected from the group consisting of platinum, palladium, rhenium and mixtures thereof on a silicaceous support; and a metallic promoter selected the group consisting of tin, rhenium and mixtures thereof, the silicaceous support being promoted with a redox promoter selected from the group consisting of: $WO_3$; $MoO_3$; $Fe_2O_3$ and $Cr_2O_3$.

U.S. Pat. No. 7,608,744 describes a process for the selective production of ethanol by vapor phase reaction of acetic acid at a temperature of about 250° C. over a hydrogenating catalyst composition either cobalt and palladium supported on graphite or cobalt and platinum supported on silica selectively produces ethanol.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process using a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; (iv) insufficient catalyst life; and/or (v) required activity for both ethyl acetate and acetic acid with decreased byproduct formation.

SUMMARY OF THE INVENTION

In a first embodiment, the present invention is directed to a hydrogenation catalyst comprising a precious metal and at least one active metal on a modified silica support, wherein the catalyst has at least 70% Lewis acid sites based on the total number of acid sites as measured by Fourier transform infrared spectroscopy of chemisorbed pyridine (FTIR), and wherein the modified silica support comprises: (i) a support material; and (ii) a support modifier comprising a metal selected from the group consisting of tungsten, molybdenum, vanadium, niobium, and tantalum. The catalyst may have at least 80% Lewis acid sites, based on the total number of acid sites, as measured by FTIR. The modified silica support may comprise cobalt tungstate. The precious metal may be selected from the group consisting of rhodium, rhenium, ruthenium, platinum, palladium, osmium, iridium and gold. The at least one active metal may be selected from the group consisting of copper, iron, vanadium, nickel, titanium, zinc, chromium, molybdenum, tungsten, tin, lanthanum, cerium, cobalt, manganese and combinations thereof. The catalyst may be prepared by: (a) impregnating a support material with a first solution to form a first impregnated support, wherein the first solution comprises a precursor to the support modifier metal selected from the group consisting of tungsten, molybdenum, niobium, vanadium, and tantalum; (b) calcining the first impregnated support to form a modified silica support; (c) impregnating the modified silica support with a second solution to form a second impregnated support, wherein the second solution comprises a precious metal precursor, and a precursor to at least one active metal; and (d) calcining the second impregnated support to form the catalyst. The first solution may further comprise a precursor to at least one active metal selected from the group consisting of copper, iron, vanadium, nickel, titanium, zinc, chromium, molybdenum, tungsten, tin, lanthanum, cerium, cobalt, manganese and combinations thereof. The precursor to at least one active metal in the first solution may be the same precursor to at least one active metal in the second solution. The support material may have no acidic acid sites prior to impregnating with the first solution.

In a second embodiment, the present invention is directed to a process for producing ethanol, comprising contacting a feedstock comprising hydrogen and acetic acid and/or ethyl acetate in a reactor at an elevated temperature in the presence of the catalyst of claim 1, under conditions effective to form ethanol. The feedstock may further comprise greater than 5 wt. % ethyl acetate. The feedstock may further comprise ethyl acetate in an amount greater than 0 wt. %, wherein acetic acid conversion is greater than 20% and ethyl acetate conversion is greater than 5%. Selectivity to diethyl ether may be less than 1%, including selectivity of acetic acid to diethyl ether and selectivity of ethyl acetate to diethyl ether. The acetic acid may be formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In a third embodiment, the present invention is directed to a hydrogenation catalyst comprising a modified silica support, and n metals, wherein n is from 2 to 6, and the metals are selected from the group consisting of rhodium, rhenium, ruthenium, platinum, palladium, osmium, iridium, copper, iron, vanadium, nickel, titanium, zinc, chromium, molybdenum, tungsten, vanadium, niobium, tantalum, tin, lanthanum, cerium, cobalt, manganese, and oxides thereof, wherein the hydrogenation catalyst has at least 70% Lewis acid sites, based on the percent of all acidic sites, as measured by FTIR of chemisorbed pyridine. In some embodiments, n is 3. The modified silica support may comprise a silica support, a support modifier, and at least one active metal. The support modifier may be selected from the group consisting of tungsten, molybdenum, niobium, vanadium, and tantalum. The at least one active metal may be selected from the group consisting of copper, iron, vanadium, nickel, titanium, zinc, chromium, molybdenum, tungsten, tin, lanthanum, cerium, cobalt, manganese and combinations thereof. The catalyst may be prepared by: (a) impregnating a support material with a first solution to form a first impregnated support, wherein the first solution comprises a precursor to a support modifier metal selected from the group consisting of tungsten, molybdenum, niobium, vanadium, and tantalum; (b) calcining the first impregnated support to form a modified silica support; (c) impregnating the modified silica support with a second solution to form a second impregnated support, wherein the second solution comprises a precursor to each of the at least one active metals; and (d) calcining the second impregnated support to form the catalyst.

BRIEF DESCRIPTION OF THE DRAWINGS

The invention may be more completely understood in consideration of the following detailed description of various embodiments of the invention in connection with the accompanying figure.

DETAILED DESCRIPTION OF THE INVENTION

Catalyst Composition

Figure 1:
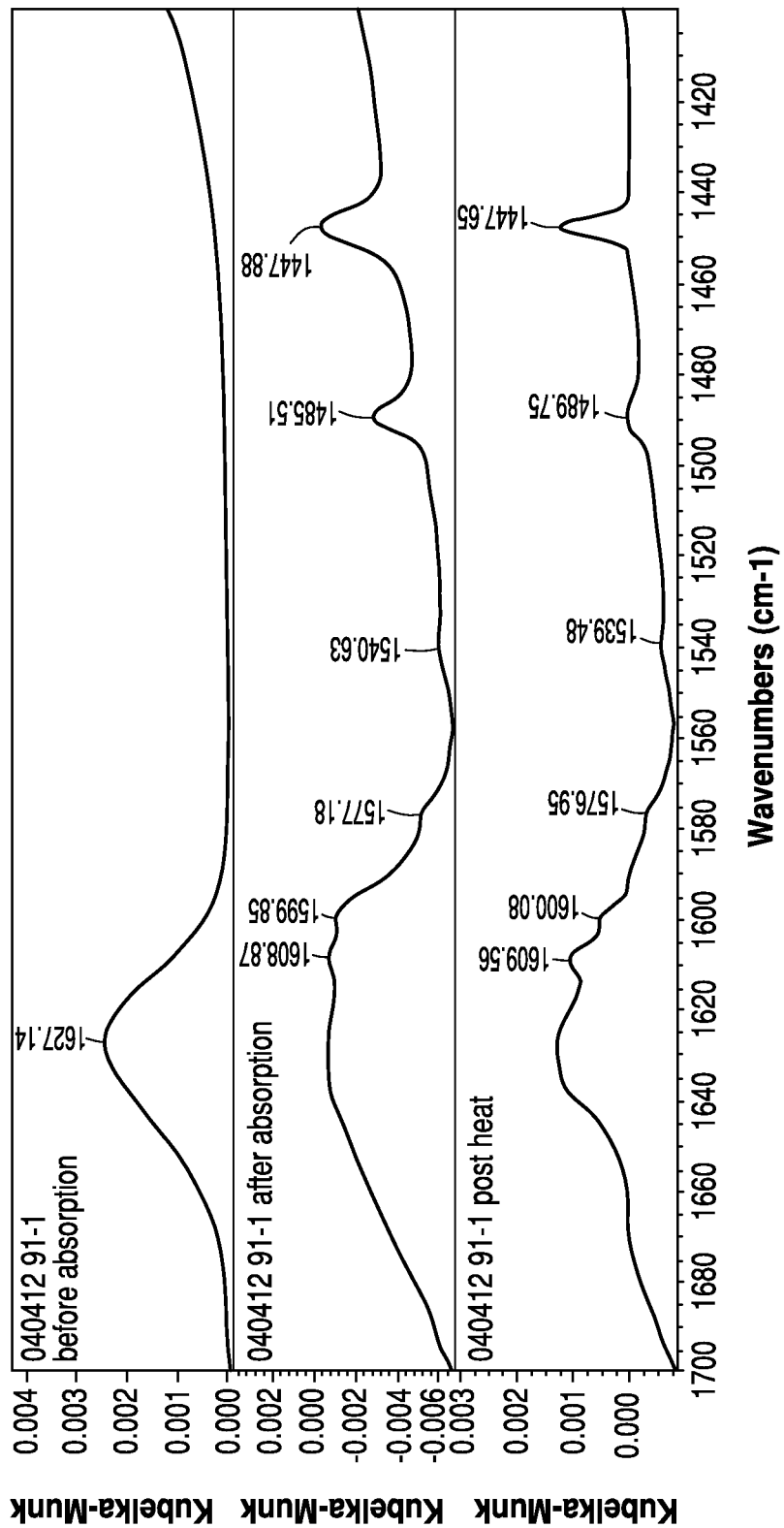
FIG. 1 shows an FTIR of chemisorbed pyridine spectra in accordance with an embodiment of the present invention.

The present invention is directed to catalyst compositions that preferably are suitable as hydrogenation catalysts, to processes for forming such catalysts, and to chemical processes employing such catalysts. The catalyst may be suitable in catalyzing the hydrogenation of a carboxylic acid, e.g., acetic acid, and/or esters thereof, e.g., ethyl acetate, to the corresponding alcohol, e.g., ethanol. The catalysts preferably have a surface acidity wherein a majority of the acidic sites are Lewis acid sites. The balance of Lewis acid to Brønsted acid sites should favor Lewis acid and lead to fewer Brønsted acid sites. For purposes of the present invention, acidic sites on the surface of the catalyst are determined by infrared spectroscopy, in particular Fourier transform infrared spectroscopy (FTIR). Unless the context indicates otherwise, the acidity of a surface or the number of acid sites thereupon may be determined by the technique described in F. Delannay, Ed., "Characterization of Heterogeneous Catalysts;" Chapter III: Measurement of Acidity of Surfaces, p. 370-404; Marcel Dekker, Inc., N.Y. 1984. Ammonia or pyridine may be used as the base, and it is preferred to use pyridine for determining surface acidity. In one embodiment, at least 70% of the acidic sites on the surface of the catalyst are Lewis acid sites, e.g., at least 80%, or at least 85%. In some embodiments, 100% of the acidic sites may be Lewis acid sites. In other embodiments, the percentage of Lewis acid sites may range from 56% to 100%, e.g., from 66% to 100%.

Surprisingly and unexpectedly, the acidic sites on the catalyst, specifically Lewis acid sites, may be at least partially responsible for an increase in conversion and selectivity to ethanol when using the catalyst for hydrogenation of a carboxylic acid and/or esters thereof. In particular, Lewis acid sites may be useful in promoting the conversion of ethyl acetate to ethanol. This is particularly advantageous when introducing mixed feeds of acetic acid and ethyl acetate into the hydrogenation reactor. Without being bound by theory, the increase of Lewis acid sites relative to Brønsted acid sites is believed to reduce certain impurities such as diethyl ether. Diethyl ether is an impurity that needs to be removed from ethanol that increases costs in purification. Diethyl ether is not readily converted to ethanol and reduces raw material productivity.

The catalysts preferably comprise a modified silica support, e.g., a modified silica support, having acidic sites. The support material, namely silica, generally has no acidic sites. Acidic sites may be introduced to silica when a support modifier is added, as described further herein. When adding the support modifier to silica it is difficult to achieve the desired balance of Lewis acid to Brønsted acid sites. In addition, because the modified silica support is not catalytically active for hydrogenation of acetic acid and/or ethyl acetate to ethanol, one or more active metal, including precious metals, needs to be added. Depending on the active metal this may change the balance of Lewis acid to Brønsted acid sites. Preferably, the active metals are added favor a majority of Lewis acid sites on the surface of the catalyst. The active metals may i) increase the number of Lewis acid sites; ii) block or suppress the availability of Brønsted acid sites by amphoteric materials such as tin oxides; iii) block or suppress the total number of acidic sites; or iv) combinations thereof. In particular tin, as an active metal, has been found to be a particular useful for achieving a favorable balance of Lewis acid sites.

Support Modifiers

To form the modified silica support, a support modifier is added to the support material. A support modifier may adjust the acidity of the support material by forming a plurality of acidic sites on the surface of the support. These acidic sites may be Lewis acid sites, Brønsted acid sites, and combinations thereof. The relative balance of Lewis to Brønsted acid sites may vary on the modified silica support. Thus, in one embodiment, the support modifier may form more Brønsted acid sites relative to the Lewis acid sites. After the active metals are added, it is preferred that the catalyst comprises more Lewis acid sites relative to Brønsted acid sites.

In one embodiment, a support modifier comprises a metal selected from the group consisting of tungsten, molybdenum, vanadium, niobium, and tantalum. The metal for the support modifier may be an oxide thereof. In one embodiment, the support modifiers are present in an amount from 0.1 wt. % to 50 wt. %, e.g., from 0.2 wt. % to 25 wt. %, from 0.5 wt. % to 20 wt. %, or from 1 wt. % to 15 wt. %, based on the total weight of the catalyst. When the support modifier comprises tungsten, molybdenum, and vanadium, the support modifier may be present in an amount from 0.1 to 40 wt. %, e.g., from 0.1 to 30 wt. % or from 0.1 to 20 wt. %, based on the total weight of the catalyst.

As indicated, the support modifiers may adjust the acidity of the support. For example, the acid sites, e.g., Brønsted acid sites or Lewis acid sites, on the support material may be adjusted by the support modifier. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts;" Chapter III: Measurement of Acidity of Surfaces, p. 370-404; Marcel Dekker, Inc., N.Y. 1984, the entirety of which is incorporated herein by reference.

In some embodiments, the support modifier may be an acidic modifier that increases the acidity of the catalyst, by forming acidic sites on a support material that lacks acidic sites, such as silica. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. In one embodiment, the support modifier comprises metal selected from the group consisting of tungsten, molybdenum, vanadium, niobium, and tantalum. In a preferred embodiment, the support modifier comprises metal selected from the group consisting of tungsten, vanadium, and tantalum. In addition, the support modifier preferably does not comprise phosphorous and is not made from a phosphorous containing precursor.

In one embodiment, the acidic modifier may also include those selected from the group consisting of $WO_3$, $MoO_3$, $V_2O_5$, $VO_2$, $V_2O_3$, $Nb_2O_5$, $Ta_2O_5$, and $Bi_2O_3$. Reduced tungsten oxides or molybdenum oxides may also be employed, such as, for example, one or more of $W_{20}O_{58}$, $WO_2$, $W_{49}O_{119}$, $W_{50}O_{148}$, $W_{18}O_{49}$, $Mo_9O_{26}$, $Mo_8O_{23}$, $Mo_5O_{14}$, $Mo_{17}O_{47}$, $Mo_4O_{11}$, or $MoO_2$. The tungsten oxide may be cubic tungsten oxide ($H_{0.5}WO_3$). In one embodiment, the use of such metal oxide support modifiers in combination with a precious metal and at least one active metal may result in catalysts having multifunctionality, and which may be suitable for converting a carboxylic acid, such as acetic acid, as well as corresponding esters thereof, e.g., ethyl acetate, to one or more hydrogenation products, such as ethanol, under hydrogenation conditions.

In other embodiments, the acidic support modifiers include those selected from the group consisting of $ZrO_2$, $Nb_2O_5$, $Ta_2O_5$, $Al_2O_3$, $B_2O_3$, $P_2O_5$, and $Sb_2O_3$. Acidic support modifiers include those selected from the group consisting of $ZrO_2$, $Nb_2O_5$, $Ta_2O_5$, and $Al_2O_3$. In addition to the support modifier, the modified silica support may also comprises at least one active metal. The at least one active metal may be selected from the group consisting of copper, iron, vanadium, nickel, titanium, zinc, chromium, molybdenum, tungsten, tin, lanthanum, cerium, cobalt, manganese and combinations thereof. In some embodiments, the at least one active metal may be cobalt and tin. The modified silica support may comprise from 0.5 to 20 wt. % cobalt, e.g., from 1 to 15 wt. % or from 1.5 to 10 wt. % and from 0.5 to 20 wt. % tin, e.g., from 1 to 15 wt. % or from 1.5 to 10 wt. %.

In some embodiments, the acidic support modifier comprises a mixed metal oxide comprising at least one of the active metals and an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, cobalt molybdate, cobalt vanadate, cobalt niobate, and/or cobalt tantalate. In one embodiment, the catalyst does not comprise and is substantially free of tin tungstate. Catalysts containing such mixed metal support modifiers may provide the desired degree of multifunctionality at increased conversion, e.g., increased ester conversion. The reduction in Brønsted acidic sites may also contribute to a decrease in byproduct formation, and in particular diethyl ether formation.

In some embodiments, the modified silica support comprises at least one active metal in addition to one or more acidic modifiers. The modified silica support may, for example, comprise at least one active metal selected from copper, iron, cobalt, vanadium, nickel, titanium, zinc, chromium, molybdenum, tungsten, tin, lanthanum, cerium, and manganese. For example, the support may comprise an active metal, preferably not a precious metal, and an acidic or basic support modifier. Preferably, the support modifier comprises a support modifier metal selected from the group consisting of tungsten, molybdenum, vanadium, niobium, and tantalum. In this aspect, the final catalyst composition comprises a precious metal, and at least one active metal disposed on the modified silica support. In a preferred embodiment, at least one of the active metals in the modified silica support is the same as at least one of the active metals disposed on the support material. For example, the catalyst may comprise a support material modified with cobalt, tin and tungsten (optionally as $WO_3$, $H_{0.5}WO_3$, $HWO_4$, and/or as cobalt tungstate). In this example, the catalyst further comprises a precious metal, e.g., palladium, platinum or rhodium, and at least one active metal, e.g., cobalt and/or tin, disposed on the modified silica support.

Without being by bound theory, it is believed that the presence of cobalt tungstate on the modified silica support or catalyst tends to decrease the Brønsted acid sites, as compared to a support modified only with tungsten oxide. When used on the modified silica support, tin oxides further reduce the Brønsted acid sites due to the amphoteric properties.

Support Materials

The catalysts of the present invention comprise a suitable support material, preferably a modified silica support. In one embodiment, the support material may be silica, including pyrogenic silica or high purity silica. Generally silica does not contain acidic sites and a support modifier is needed to added acidic sites. In other embodiments, the support material may be silica/alumina that may contain some acidic sites. In one embodiment the support material is substantially free of alkaline earth metals, such as magnesium and calcium. The support material is present in an amount from 25 wt. % to 99 wt. %, e.g., from 30 wt. % to 98 wt. % or from 35 wt. % to 95 wt. %, based on the total weight of the catalyst.

In preferred embodiments, the support material comprises silica having a surface area of at least 50 $m^2/g$, e.g., at least 100 $m^2/g$, or at least 150 $m^2/g$. In terms of ranges, the support material preferably has a surface area from 50 to 600 $m^2/g$. For purposes of the present specification, surface area refers to BET nitrogen surface area, meaning the surface area as determined by ASTM D6556-04, the entirety of which is incorporated herein by reference.

The preferred support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 $cm^3/g$, e.g., from 0.7 to 1.5 $cm^3/g$ or from 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the precious metal and the cobalt and/or tin that are disposed on the support are generally in the form of very small metal (or metal oxide) particles or crystallites relative to the size of the support, these metals should not substantially impact the size of the overall catalyst particles. Thus, the above particle sizes generally apply to both the size of the modified silica support as well as to the final catalyst particles, although the catalyst particles are preferably processed to form much larger catalyst particles, e.g., extruded to form catalyst pellets.

Active Metals

The catalyst comprises one or more active metals on the modified silica support. Once the active metals are added to the modified silica support, the majority of acidic sites are Lewis acid sites as discussed herein. The active metals may be selected from the group consisting of rhodium, rhenium, ruthenium, platinum, palladium, osmium, iridium, nickel, titanium, zinc, chromium, molybdenum, tungsten, vanadium, niobium, tantalum, tin, lanthanum, cerium, cobalt, manganese, and oxides thereof. Preferably, there are combinations of at least two, or at least three of the active metals. The number of active metals may range from 2 to 6, but additional active metals may also be included. In one embodiment, the active metals may be selected from the group consisting of rhodium, rhenium, ruthenium, platinum, palladium, osmium, iridium, nickel, titanium, zinc, chromium, molybdenum, tungsten, vanadium, niobium, tantalum, tin, lanthanum, cerium, cobalt, manganese, and oxides thereof provided that at least two of the two or more metals include platinum, palladium, molybdenum, tungsten, tin, cobalt, and oxides thereof.

The total weight of all the active metals, including the aforementioned precious metal, present in the catalyst preferably is from 0.1 to 25 wt. %, e.g., from 0.5 to 15 wt. %, or from 1.0 to 10 wt. %. In one embodiment, the catalyst may comprise from cobalt in an amount from 0.5 to 20 wt. % and tin in an amount from 0.5 to 20 wt. %. The active metals for purposes of the present invention may be disposed on the modified silica support. For purposes of the present specification, unless otherwise indicated, weight percent is based on the total weight the catalyst including metal and support.

In one embodiment, the active metals may include at least one precious metal selected from the group consisting of rhodium, rhenium, ruthenium, platinum, palladium, osmium, iridium gold, and oxides or combinations thereof. In terms of ranges, the catalyst may comprise the precious metal in an amount from 0.05 to 10 wt. %, e.g. from 0.1 to 5 wt. %, or from 0.1 to 3 wt. %, based on the total weight of the catalyst. In some embodiments, the metal loading of the precious metal may be less than the metal loadings of the one or more active metals. When a precious metal is used, the other active metal or oxides thereof may be selected from the group consisting of copper, iron, vanadium, nickel, titanium, zinc, chromium, molybdenum, tungsten, tin, lanthanum, cerium, cobalt, manganese and combinations thereof.

Preferred bimetallic (precious metal+active metal) combinations for some exemplary catalyst compositions include platinum/tin, platinum/ruthenium, platinum/rhenium, platinum/nickel, palladium/ruthenium, palladium/rhenium, palladium/copper, palladium/nickel, gold/palladium, ruthenium/rhenium, ruthenium/iron, rhodium/iron, rhodium/nickel and rhodium/tin. In some embodiments, the catalyst comprises three metals on a support, e.g., one precious metal and two active metals. Exemplary tertiary combinations may include palladium/rhenium/tin, palladium/rhenium/nickel, platinum/tin/palladium, platinum/tin/rhodium, platinum/tin/gold, platinum/tin/iridium, platinum/tin/copper, platinum/tin/chromium, platinum/tin/zinc, platinum/tin/nickel, rhodium/nickel/tin, and rhodium/iron/tin.

In one embodiment, the catalyst comprises from 0.25 to 1.25 wt. % platinum, and from 1 to 5 wt. % tin on a modified silica support. The support material comprises silica or silica-alumina. The cobalt is disposed on the support material along with a support modifier. The modified silica support may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %. At least 85% of the acidic sites on the support are Lewis acid sites.

In another embodiment, the catalyst comprises from 0.25 to 2.5 wt. % platinum, and from 1 to 5 wt. % tin on a modified silica support. The support material comprises silica or silica-alumina. The cobalt and/or tin are disposed on the support material along with a support modifier. The modified silica support may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %. At least 85% of the acidic sites on the support are Lewis acid sites.

Processes for Making the Catalyst

The present invention also relates to processes for making the catalyst. In one embodiment, the support material is modified with one or more support modifiers and the resulting modified silica support is subsequently impregnated with a precious metal and at least one active metal to form the catalyst composition. It should be understood that precursors may be used to added or impregnated the support material or modified silica support. For example, the support material may be impregnated with a support modifier solution, e.g., first solution, comprising a precursor to the support modifier and optionally one or more active metal precursors, such as cobalt and tin, to form the modified silica support. After drying and calcination, the resulting modified silica support is impregnated with a second solution comprising precious metal precursor and one or more active metal precursors, to form a second impregnated support, followed by drying and calcination to form the final catalyst.

The precursors preferably are comprised of salts of the respective metals in solution, which, when heated, are converted to elemental metallic form or to a metal oxide. In some embodiments, cobalt and/or tin precursors are impregnated onto the support material simultaneously and/or sequentially with the support modifier precursor, and cobalt and/or tin may interact with the support modifier metal at a molecular metal upon formation to form one or more polymetallic crystalline species, such as cobalt tungstate. In other embodiments, cobalt and/or tin will not interact with the support modifier metal precursor and are separately deposited on the support material, e.g., as discrete metal nanoparticles or as an amorphous metal mixture. Thus, the support material may be modified with one or more cobalt and/or tin precursors at the same time that it is modified with a support modifier metal, and cobalt and/or tin may or may not interact with the support modifier metal to form one or more polymetallic crystalline species.

In some embodiments, the support modifier may be added as particles to the support material. For example, one or more support modifier precursors, if desired, may be added to the support material by mixing the support modifier particles with the support material, preferably in water to form a slurry. When mixed it is preferred for some support modifiers to use a powdered material of the support modifiers. If a powdered material is employed, the support modifier may be pelletized, crushed and sieved prior to being added to the support.

The support modifier may be added through a wet impregnation step using a support modifier precursor. Some exemplary support modifier precursors include alkali metal oxides, alkaline earth metal oxides, Group IIB metal oxides, Group IIIB metal oxides, Group IVB metal oxides, Group VB metal oxides, Group VIB metal oxides, Group VIIB metal oxides, and/or Group VIII metal oxides, as well as preferably aqueous salts thereof.

Although the overwhelming majority of metal oxides and polyoxoion salts are insoluble, or have a poorly defined or limited solution chemistry, the class of isopoly- and heteropolyoxoanions of the early transition elements forms an important exception. These complexes may be represented by the general formulae:

$[M_mO_y]^{p-}$ Isopolyanions $[X_xM_mO_y]^{q-} (x \leq m)$ Heteropolyanions where M is selected from tungsten, molybdenum, vanadium, niobium, tantalum and mixtures thereof, in their highest ($d^0$, $d^1$) oxidations states. Such polyoxometalate anions form a structurally distinct class of complexes based predominately, although not exclusively, upon quasi-octahedrally-coordinated metal atoms. The elements that can function as the addenda atoms, M, in heteropoly- or isopolyanions may be limited to those with both a favorable combination of ionic radius and charge and the ability to form $d_\pi$-$p_\pi$ M-O bonds. There is little restriction, however, on the heteroatom, X, which may be selected from virtually any element other than the rare gases. See, e.g., M. T. Pope, *Heteropoly and Isopoly Oxometalates*, Springer Verlag, Berlin, 1983, 180; Chapt. 38, *Comprehensive Coordination Chemistry*, Vol. 3, 1028-58, Pergamon Press, Oxford, 1987, the entireties of which are incorporated herein by reference.

Polyoxometalates (POMs) and their corresponding heteropoly acids (HPAs) have several advantages making them economically and environmentally attractive. First, HPAs have a very strong approaching the superacid region, Brønsted acidity. In addition, they are efficient oxidants exhibiting fast reversible multielectron redox transformations under rather mild conditions. Solid HPAs also possess a discrete ionic structure, comprising fairly mobile basic structural units, e.g., heteropolyanions and countercations ($H^+$, $H_3O^+$, $H_5O_2^+$, etc.), unlike zeolites and metal oxides.

In view of the foregoing, in some embodiments, the support modifier precursor comprises a POM, which preferably comprises a metal selected from the group consisting of tungsten, molybdenum, niobium, vanadium and tantalum. In some embodiments, the POM comprises a hetero-POM. A non-limiting list of suitable POMs includes phosphotungstic acid (H-$PW_{12}$) ($H_3PW_{12}O_{40}.nH_2O$), ammonium metatungstate (AMT) (($NH_4)_6H_2W_{12}O_{40}.H_2O$), ammonium heptamolybdate tetrahydrate, (AHM) (($NH_4)_6Mo_7O_{24}.4H_2O$), silicotungstic acid hydrate (H—$SiW_{12}$) ($H_4SiW_{12}O_{40}.H_2O$), silicomolybdic acid (H—$SiMo_{12}$) ($H_4SiMo_{12}O_{40}.nH_2O$), and phosphomolybdic acid (H—$PMo_{12}$) ($H_3PMo_{12}O_{40}.nH_2O$).

The use of POM-derived support modifiers in the catalyst compositions of the invention has now surprising and unexpectedly been shown to provide bi- or multi-functional catalyst functionality, desirably resulting in conversions for both acetic acid and byproduct esters such as ethyl acetate, thereby rendering them suitable for catalyzing mixed feeds comprising, for example, acetic acid and ethyl acetate.

When the modified silica support further comprises at least one active metal, the first solution may comprise a precursor to at least one active metal selected from the group consisting of copper, iron, vanadium, nickel, titanium, zinc, chromium, molybdenum, tungsten, tin, lanthanum, cerium, cobalt, manganese and combinations thereof. In some embodiments, the at least one active metal in the first solution is the same as the at least one active metal in the second solution.

Impregnation of the precious metal and the at least one active metal onto the modified silica support, may occur simultaneously (co-impregnation) or sequentially. In simultaneous impregnation, the two or more metal precursors are mixed together and added to the support, preferably modified silica support, together followed by drying and calcination to form the final catalyst composition. With simultaneous impregnation, it may be desired to employ a dispersion agent, surfactant, or solubilizing agent, e.g., ammonium oxalate or an acid such as acetic or nitric acid, to facilitate the dispersing or solubilizing of the metal precursors in the event the precursors are incompatible with the desired solvent, e.g., water.

In sequential impregnation, the first metal precursor may be added to the modified silica support followed by drying and calcining, and the resulting material may then be impregnated with the remaining metal precursor each followed by an additional drying step and calcining step to form the final catalyst composition. Additional metal precursors may be added in a similar manner. Of course, combinations of sequential and simultaneous impregnation may be employed if desired.

In embodiments where the precious metal and the at least one active metal are applied to the catalyst in multiple sequential impregnation steps, the catalyst may be said to comprise a plurality of "theoretical layers." For example, where a first metal is impregnated onto a support followed by impregnation of a second metal, the resulting catalyst may be said to have a first theoretical layer comprising the first metal and a second theoretical layer comprising the second metal. As discussed above, in some aspects, more than one cobalt and/or tin precursor may be co-impregnated onto the support in a single step such that a theoretical layer may comprise more than one metal or metal oxide. In another aspect, the same metal precursor may be impregnated in multiple sequential impregnation steps leading to the formation of multiple theoretical layers containing the same metal or metal oxide. In this context, notwithstanding the use of the term "layers," it will be appreciated by those skilled in the art that multiple layers may or may not be formed on the catalyst support depending, for example, on the conditions employed in catalyst formation, on the amount of metal used in each step and on the specific metals employed.

The use of a solvent, such as water, glacial acetic acid, a strong acid such as hydrochloric acid, nitric acid, or sulfuric acid, or an organic solvent, is preferred in the support modification step, e.g., for impregnating a support modifier precursor onto the support material. The support modifier solution comprises the solvent, preferably water, a support modifier precursor, and preferably one or more cobalt and/or tin precursors. The solution is stirred and combined with the support material using, for example, incipient wetness techniques in which the support modifier precursor is added to a support material having the same pore volume as the volume of the solution. Impregnation occurs by adding, optionally drop wise, a solution containing the precursors of either or both the support modifier metals, cobalt and/or tin, to the dry support material. Capillary action then draws the support modifier into the pores of the support material. The thereby impregnated support can then be formed by drying, optionally under vacuum, to drive off solvents and any volatile components within the support mixture and depositing the support modifier on and/or within the support material. Drying may occur, for example, at a temperature from 50° C. to 300° C. for a period from 1 to 24 hours. The dried support may be calcined optionally with ramped heating, for example, at a temperature from 300° C. to 900° C. for a period of time from 1 to 12 hours to form the final modified silica support. Upon heating and/or the application of vacuum, the metal(s) of the precursor(s) preferably decompose into their oxide or elemental form. In some cases, the completion of removal of the solvent may not take place until the catalyst is placed into use and/or calcined, e.g., subjected to the high temperatures encountered during operation. During the calcination step, or at least during the initial phase of use of the catalyst, such compounds are converted into a catalytically active form of the metal or a catalytically active oxide thereof.

Once formed, the modified silica supports may be shaped into particles having the desired size distribution, e.g., to form particles having an average particle size in the range from 0.2 to 0.4 cm. The supports may be extruded, pelletized, tabletized, pressed, crushed or sieved to the desired size distribution. Any of the known methods to shape the support materials into desired size distribution can be employed. Alternatively, support pellets may be used as the starting material used to make the modified silica support and, ultimately, the final catalyst.

In one embodiment, the catalyst of the present invention may be prepared using a bulk catalyst technique. Bulk catalysts may be formed by precipitating precursors to support modifier metals, cobalt and/or tin. The precipitating may be controlled by changing the temperature, pressure, and/or pH. In some embodiments, the bulk catalyst preparation may use a binder. A support material may not be used in a bulk catalyst process. Once precipitated, the bulk catalyst may be shaped by spraying drying, pelleting, granulating, tablet pressing, beading, or pilling. Suitable bulk catalyst techniques may be used such as those described in Krijn P. de Jong, ed., Synthesis of Solid Catalysts, Wiley, (2009), pg. 308, the entire contents and disclosure of which is incorporated by reference.

In one embodiment, the precious metal and the at least one active metal are impregnated onto the support, preferably onto any of the above-described modified silica supports. A precursor of the precious metal preferably is used in the metal impregnation step, such as a water soluble compound or water dispersible compound/complex that includes the precious metal of interest. Similarly, one or more precursors to cobalt and/or tin may also be impregnated into the support, preferably modified silica support. Depending on the metal precursors employed, the use of a solvent, such as water, glacial acetic acid, nitric acid or an organic solvent, may be preferred to solubilize the metal precursors.

In one embodiment, separate solutions of the metal precursors are formed, which are subsequently blended prior to being impregnated on the support material. For example, a first solution may be formed comprising a first metal precursor, and a second solution may be formed comprising a second metal precursor and optionally a third metal precursor. At least one of the first, second and optional third metal precursors preferably is a precious metal precursor, and the other(s) are preferably cobalt and/or tin precursors (which may or may not comprise precious metal precursors). Either or both solutions preferably comprise a solvent, such as water, glacial acetic acid, hydrochloric acid, nitric acid or an organic solvent.

In one exemplary embodiment, a first solution comprising a first metal halide is prepared. In some embodiments, the first metal halide comprises a tin halide, e.g., a tin chloride such as tin (II) chloride and/or tin (IV) chloride. A second metal precursor, as a solid or as a separate solution, is combined with the first solution to form a combined solution. In some embodiments, the second metal precursor comprises a cobalt oxalate, acetate, halide or nitrate. A second solution is also prepared comprising a precious metal precursor, such as a halide of rhodium, rhenium, ruthenium, platinum or palladium. The second solution is combined with the combined solution to form a mixed metal precursor solution. The resulting mixed metal precursor solution may then be added to the modified silica support, followed by drying and calcining to form the final catalyst composition as described above. The resulting catalyst may or may not be washed after the final calcination step. Due to the difficulty in solubilizing some precursors, it may be desired to reduce the pH of the first and/or second solutions, for example by employing an acid such as acetic acid, hydrochloric acid or nitric acid, e.g., 6 to 10 M HNO$_3$.

In another aspect, a first solution comprising a first metal oxalate is prepared, such as an oxalate of cobalt and/or tin. In this embodiment, the first solution preferably further comprises an acid such as acetic acid, hydrochloric acid, phosphoric acid or nitric acid, e.g., 6 to 10 M HNO$_3$. A second metal precursor, as a solid or as a separate solution, is combined with the first solution to form a combined solution. The second metal precursor, if used, preferably comprises cobalt oxalate, acetate, halide or nitrate. A second solution is also formed comprising a precious metal oxalate, for example, an oxalate of rhodium, rhenium, ruthenium, platinum or palladium, and optionally further comprises an acid such as acetic acid, hydrochloric acid, phosphoric acid or nitric acid, e.g., 6 to 10 M HNO$_3$. The second solution is combined with the combined solution to form a mixed metal precursor solution. The resulting mixed metal precursor solution may then be added to the modified silica support, followed by drying and calcining to form the final catalyst composition as described above. The resulting catalyst may or may not be washed after the final calcination step.

In one embodiment, the impregnated modified silica support is dried at a temperature from 100° C. to 140° C. for 1 to 12 hours. If calcination is desired, it is preferred that the calcination temperature employed in this step is less than the calcination temperature employed in the formation of the modified silica support, discussed above. The second calcination step, for example, may be conducted at a temperature that is at least 50° C. less than the first calcination step. For example, the impregnated catalyst may be calcined at a temperature from 200° C. to 500° C., for a period from 1 to 12 hours.

In one embodiment, ammonium oxalate is used to solubilize at least one of the metal precursors, e.g., a tin precursor, as described in U.S. Pat. No. 8,211,821, the entirety of which is incorporated herein by reference. In this aspect, a solution of the second metal precursor may be made in the presence of ammonium oxalate as solubilizing agent, and the precious metal precursor may be added thereto, optionally as a solid or a separate solution. If used, the third metal precursor may be combined with the solution comprising the first precursor and tin oxalate precursor, or may be combined with the second metal precursor, optionally as a solid or a separate solution, prior to addition of the first metal precursor. In other embodiments, an acid such as acetic acid, hydrochloric acid or nitric acid may be substituted for the ammonium oxalate to facilitate solubilizing of the tin oxalate. The resulting mixed metal precursor solution may then be added to the modified silica support followed by drying and calcining to form the final catalyst composition as described above.

The specific precursors used in the various embodiments of the invention may vary widely. Suitable metal precursors may include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, sodium platinum chloride, and platinum ammonium nitrate, Pt(NH$_3$)$_4$(NO$_4$)$_2$. Generally, both from the point of view of economics and environmental aspects, aqueous solutions of soluble compounds of platinum and palladium are preferred. In one embodiment, the precious metal precursor is not a metal halide and is substantially free of metal halides, while in other embodiments, as described above, the precious metal precursor is a halide.

In another example, cobalt and/or tin are co-impregnated with the tungsten precursor on the support material and may form a mixed oxide with WO$_3$, e.g., cobalt tungstate, followed by drying and calcination. The resulting modified silica support may be impregnated, preferably in a single impregnation step or multiple impregnation steps, with one or more of the precious metals, cobalt and/or tin followed by a second drying and calcination step. In this manner, cobalt tungstate may be formed on the modified silica support. Again, the temperature of the second calcining step preferably is less than the temperature of the first calcining step.

Use of Catalyst to Hydrogenate Acetic Acid and Ethyl Acetate

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

After the drying and calcining of the catalyst is completed, the catalyst may be reduced in order to activate it. Reduction is carried out in the presence of a reducing gas, preferably hydrogen. The reducing gas is optionally continuously passed over the catalyst at an initial ambient temperature that is increased up to 400° C. In one embodiment, the reduction is carried out after the catalyst has been loaded into the reaction vessel where the hydrogenation will be carried out. The Lewis acid sites on the catalyst should be stable so that they are not reduced under the hydrogenation conditions.

In one embodiment the invention is to a process for producing ethanol by hydrogenating a feed stream comprising compounds selected from acetic acid, ethyl acetate and mixtures thereof in the presence of any of the above-described catalysts. In some embodiments, the feed stream may comprise at least 5 wt. % ethyl acetate, e.g., at least 10 wt. % or at least 15 wt. %. One particular preferred reaction is to make ethanol from acetic acid. The hydrogenation reaction may be represented as follows:

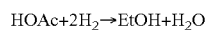

HOAc+2H$_2$→EtOH+H$_2$O

In some embodiments, the catalyst may be characterized as a bifunctional catalyst in that it effectively catalyzes the hydrogenation of acetic acid to ethanol as well as the conversion of ethyl acetate to one or more products, preferably ethanol.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Black liquor, which is an aqueous solution of lignin residues, hemicellulose, and inorganic chemicals, may also be used as a biomass source. Biomass-derived syngas has a detectable $^{14}C$ isotope content as compared to fossil fuels such as coal or natural gas.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. The microorganism employed in the fermentation process may be *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, the feed stream comprises acetic acid and ethyl acetate. A suitable acetic acid feed stream comprises one or more of the compounds selected from the group consisting of acetic acid, acetic anhydride, acetaldehyde, ethyl acetate, diethyl acetal, diethyl ether, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles. In some embodiments, multiple catalyst beds are employed in the same reactor or in different reactors, e.g., in series. For example, in one embodiment, a first catalyst functions in a first catalyst stage as a catalyst for the hydrogenation of a carboxylic acid, e.g., acetic acid, to its corresponding alcohol, e.g., ethanol, and a second bifunctional catalyst is employed in the second stage for converting unreacted acetic acid to ethanol as well as converting byproduct ester, e.g., ethyl acetate, to additional products, preferably to ethanol. The catalysts of the invention may be employed in either or both the first and/or second stages of such reaction systems.

The hydrogenation in the reactor may be carried out in either the liquid phase or vapor phase. Preferably, the reaction is carried out in the vapor phase under the following conditions. The reaction temperature may range from 125° C. to 350° C. The pressure may range from 10 kPa to 3000 kPa, e.g., from 50 kPa to 2500 kPa. The reactants may be fed to the reactor at a gas hourly space velocity that may range from 50 $hr^{-1}$ to 50,000 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1. Most preferably, the molar ratio of hydrogen to acetic acid is greater than 2:1, e.g., greater than 4:1 or greater than 8:1. For a mixed feed stream, the molar ratio of hydrogen to ethyl acetate may be greater than 5:1, e.g., greater than 10:1 or greater than 15:1.

Contact or residence time can also vary widely, depending upon such variables as amount of feed stream (acetic acid and/or ethyl acetate), catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In particular, by employing the catalysts of the invention, the hydrogenation of acetic acid and/or ethyl acetate may achieve favorable conversion and favorable selectivity and productivity to ethanol in the reactor. For purposes of the present invention, the term "conversion" refers to the amount of acetic acid or ethyl acetate, whichever is specified, in the feed that is converted to a compound other than acetic acid or ethyl acetate, respectively. Conversion is expressed as a percentage based on acetic acid or ethyl acetate in the feed. The acetic acid conversion may be at least 75%, more preferably at least 80%, at least 90%, at least 95%, or at least 99%.

During the hydrogenation of acetic acid, ethyl acetate may be produced as a byproduct. Without consuming any ethyl acetate from the mixed vapor phase reactants, the concentration of ethyl acetate in the crude product would be higher than the concentration of ethyl acetate in the feed stream. Some of the catalysts described herein are monofunctional in nature and are effective for converting acetic acid to ethanol, but not for converting ethyl acetate. The use of monofunctional catalysts may result in the undesirable build up of ethyl acetate in the system, particularly for systems employing one or more recycle streams that contain ethyl acetate to the reactor.

The preferred catalysts of the invention, however, are multifunctional in that they effectively catalyze the conversion of acetic acid to ethanol as well as the conversion of an alkyl acetate, such as ethyl acetate, to one or more products other than that alkyl acetate. The multifunctional catalyst is preferably effective for consuming ethyl acetate at a rate sufficiently great so as to at least offset the rate of ethyl acetate production, thereby resulting in non-net production of ethyl acetate. The use of such catalysts may result, for example, in an ethyl acetate conversion that is greater than 5%. In some embodiments, when the feedstock comprises ethyl acetate in an amount greater than 0%, ethyl acetate conversion is greater than 5% and acetic acid conversion is greater than 20%.

In continuous processes, the ethyl acetate being added (e.g., recycled) to the hydrogenation reactor and ethyl acetate leaving the reactor in the crude product preferably approaches a certain level after the process reaches equilibrium. The use of a multifunctional catalyst that catalyzes the conversion of ethyl acetate as well as acetic acid results in a lower amount of ethyl acetate added to the reactor and less ethyl acetate produced relative to monofunctional catalysts. In preferred embodiments, the concentration of ethyl acetate in the mixed feed and crude product is less than 40 wt. %, less than 25 wt. % or less than 15 wt. %, after equilibrium has been achieved. In preferred embodiments, the process forms a crude product comprising ethanol and ethyl acetate, and the crude product has an ethyl acetate steady state concentration from 0.1 to 40 wt. %, e.g., from 0.1 to 20 wt. % or from 0.1 to 15 wt. %.

Although catalysts that have high acetic acid conversions are desirable, such as at least 75%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid and/or ethyl acetate. It should be understood that each compound converted from acetic acid and/or ethyl acetate has an independent selectivity and that selectivity is independent of conversion. For example, if 60 mole % of the converted acetic acid is converted to ethanol, we refer to the ethanol selectivity as 60%. For purposes of the present invention, the total selectivity is based on the combined converted acetic acid and ethyl acetate. Preferably, total selectivity to ethanol is at least 60%, e.g., at least 70%, or at least 80%, at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. Productivity may range from 100 to 3,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water.

As described herein, the inventive catalysts result in low selectivity of acetic acid or ethyl acetate to diethyl ether. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Diethyl Ether | 0 to 3 | 0 to 1 | 0 to 0.5 | 0 to 0.2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.1 wt. % to 15 wt. %, from 0.1 wt. % to 10 wt. % or from 0.1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. The industrial grade ethanol may have a water concentration of less than 12 wt. % water, e.g., less than 8 wt. % or less than 3 wt. %. In some embodiments, when further water separation is used, the ethanol product preferably contains ethanol in an amount that is greater than 96 wt. %, e.g., greater than 98 wt. % or greater than 99.5 wt. %. The ethanol product having further water separation preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in U.S. Pub. Nos. 2010/0030002 and 2010/0030001 and WO2010146332, the entire contents and disclosures of which are hereby incorporated by reference.

The following examples describe the catalyst and process of this invention.

EXAMPLES

Example 1

A silica support, modified with cobalt, tin and tungsten, was tested using pyridine as a probe molecule to study whether the acidic sites were Lewis acid sites or Brønsted acid sites. The silica support was pretreated with pyridine at 200° C., for 6 hours, under vacuum. Prior to being used to pretreat the silica support, the pyridine liquid was pretreated by using a freeze-drying process to remove any moisture. Pyridine adsorption testing was conducted under room temperature, approximately 21° C., for 15 hours. The silica support was then treated again at 120° C., for 2.5 hours, under vacuum to remove any loosely adsorbed pyridine. The adsorption was measured using FTIR of chemisorbed pyridine. The FTIR spectra for this Example is shown in FIG. 1. Post heat treatment shows 78% Lewis acid sites.

Example 2

Figure 2:
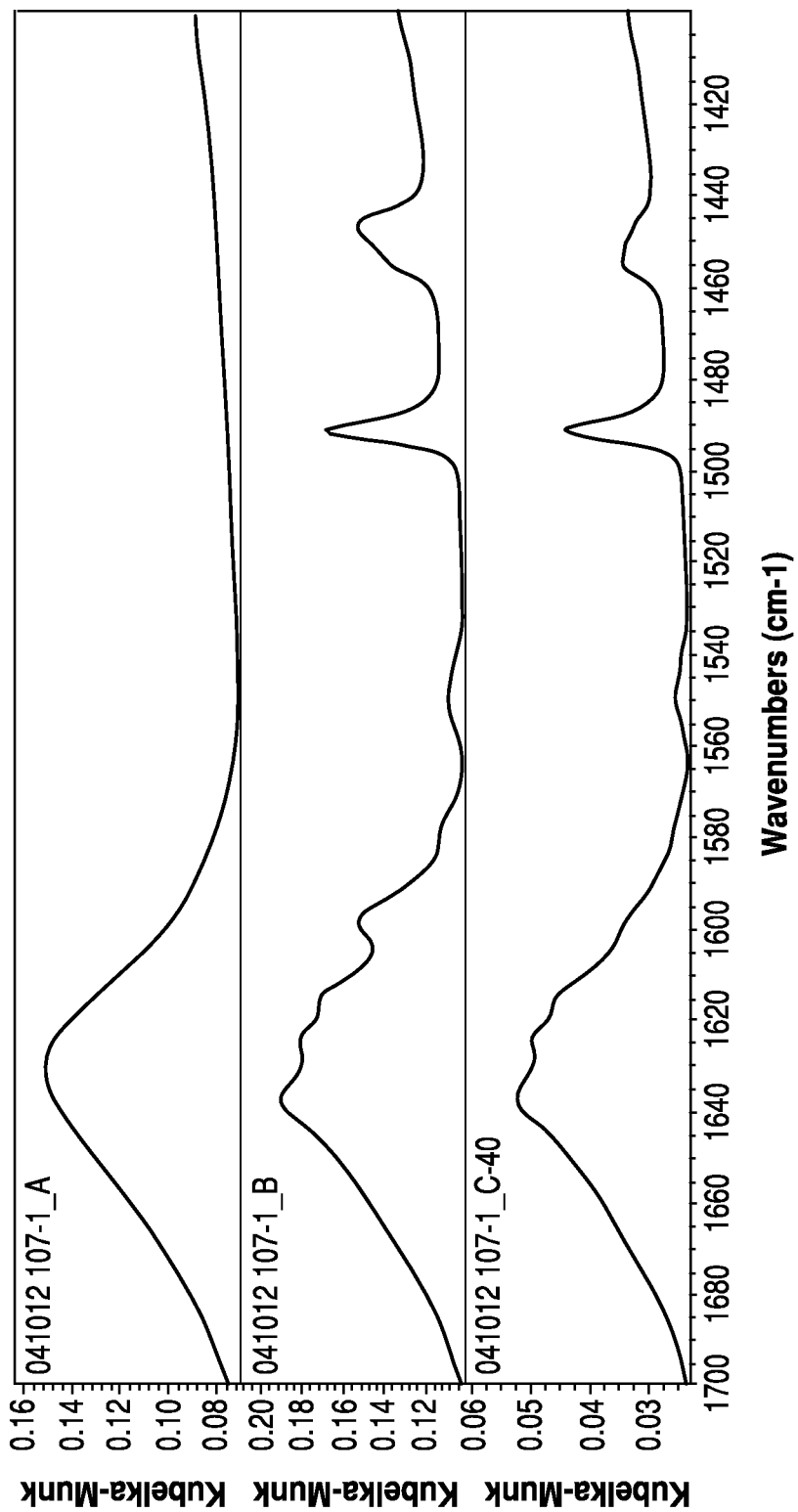
FIG. 2 shows an FTIR of chemisorbed pyridine spectra in accordance with an embodiment of the present invention.

The example was prepared and tested as in Example 1, except that the silica support was modified with alumina, calcined, and then impregnated with platinum and tin. The FTIR spectra for this Example is shown in FIG. 2. Post heat treatment shows 66% Lewis acid sites.

Example 3

Figure 3:
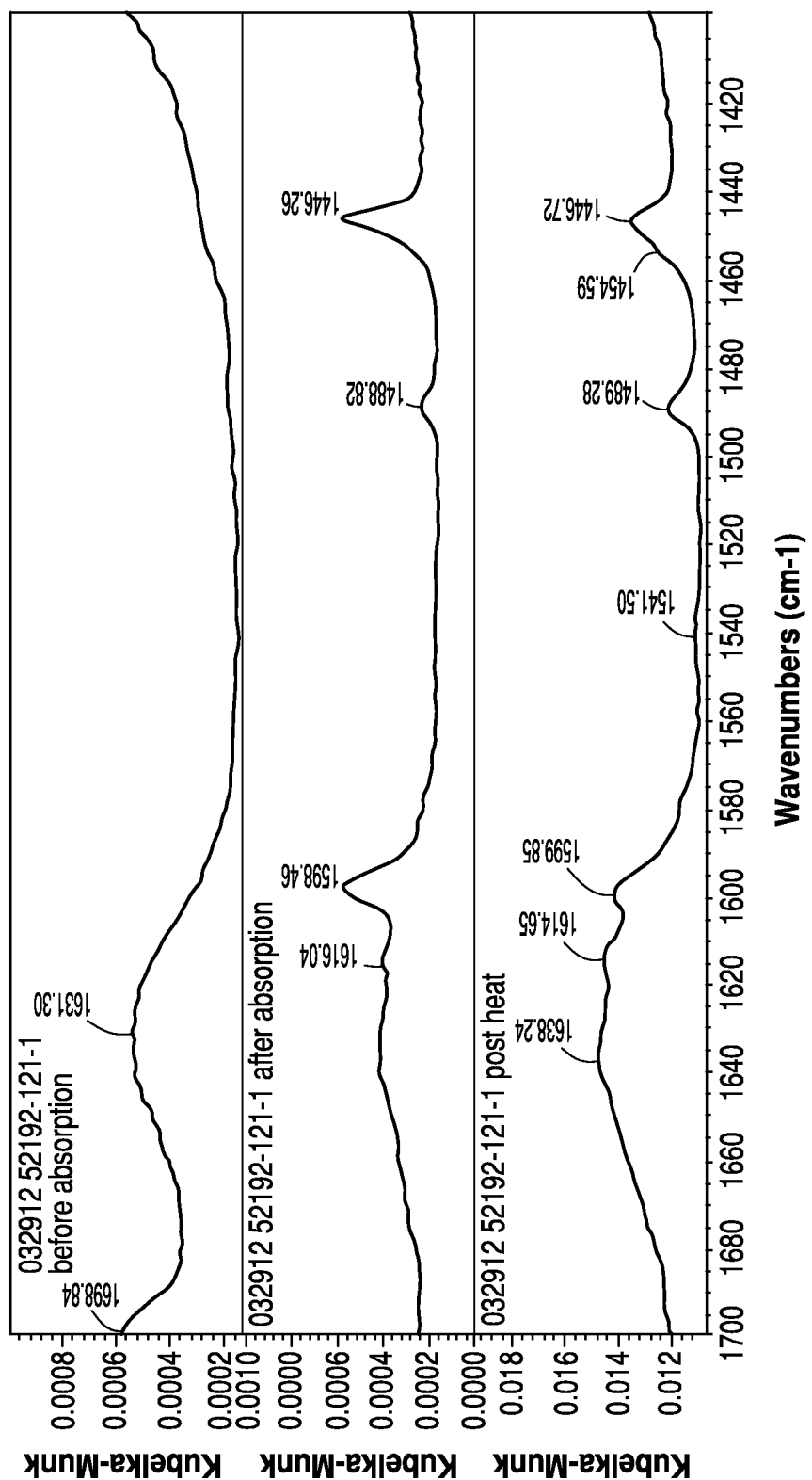
FIG. 3 shows an FTIR of chemisorbed pyridine spectra in accordance with an embodiment of the present invention.

The example was prepared and tested as in Example 1, except that the silica support was modified with tungsten oxide, calcined, and then impregnated with platinum and tin. The FTIR spectra for this Example is shown in FIG. 3. Post heat treatment shows 87% Lewis acid sites.

Example 4

Figure 4:
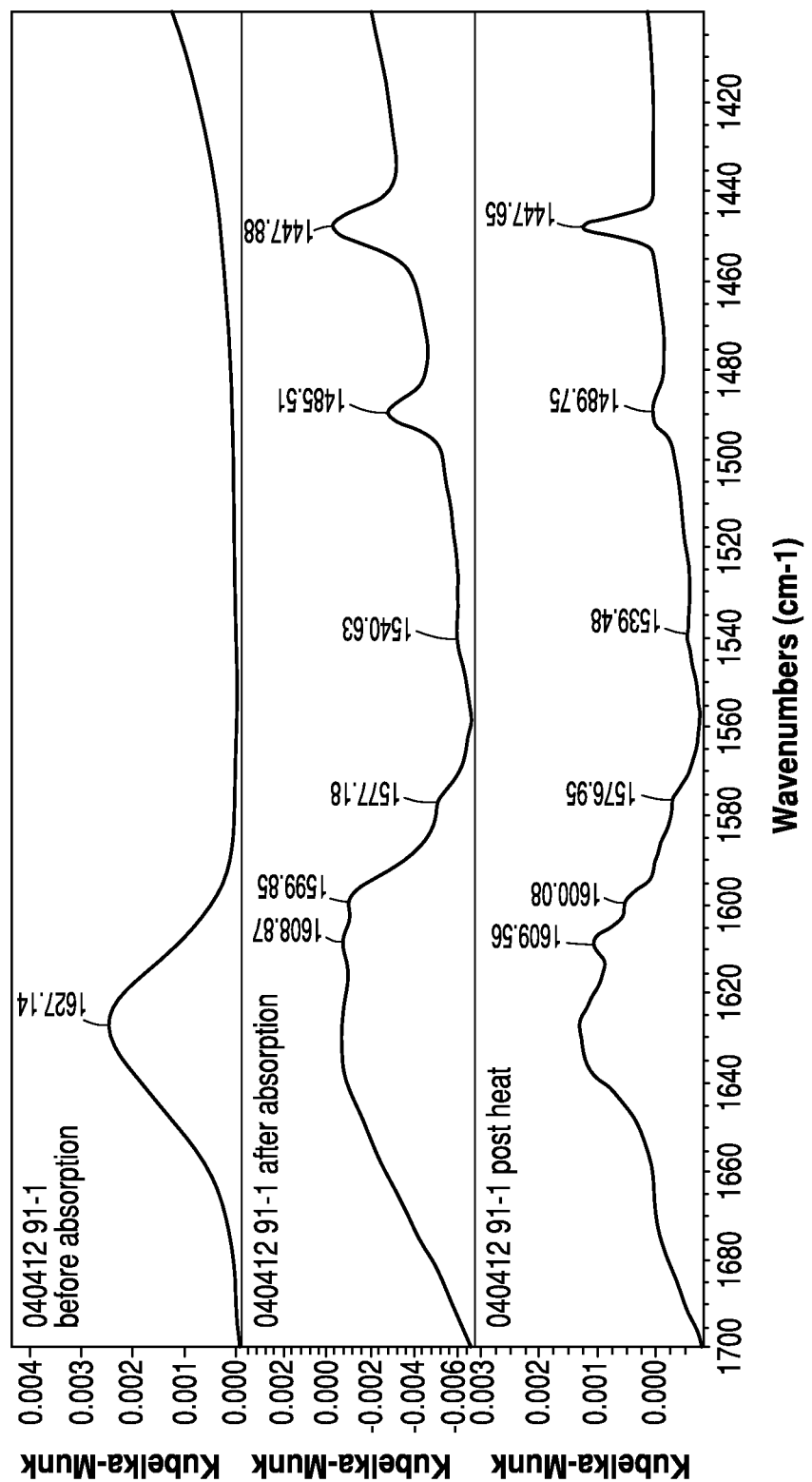
FIG. 4 shows an FTIR of chemisorbed pyridine spectra in accordance with an embodiment of the present invention.

The example was prepared and tested as in Example 1, except that the silica support was modified with cobalt, tin, and tungsten, calcined, and then impregnated with platinum and tin. The FTIR spectra for this Example is shown in FIG. 4. Post heat treatment shows 100% Lewis acid sites.

Comparative Example A

The example was prepared and tested as in Example 1, except that the silica support was not modified or impregnated with any metals.

Comparative Example B

The example was prepared and tested as in Example 1, except that the silica support was modified with calcium metasilicate, calcined, and then impregnated with platinum and tin.

Comparative Example C

The example was prepared and tested as in Example 1, except that the silica support was modified with tungsten oxide.

The results of analysis of the FTIR spectra for Examples 1-4 and Comparative Examples A-C are shown below.

TABLE 2

ACIDIC SITE ANALYSIS

|  | Lewis Acid Sites | Brønsted Acid Sites |
| --- | --- | --- |
| Example 1 | 78% | 22% |
| Example 2 | 66% | 34% |
| Example 3 | 87% | 13% |
| Example 4 | 100% | 0% |
| Comparative Example A | — | — |
| Comparative Example B | — | — |
| Comparative Example C | 46% | 54% |

The catalysts of Examples 2, 3, and 4 were fed to a test unit using one of the following running conditions.

The test unit comprised four independent tubular fixed bed reactor systems with common temperature control, pressure and gas and liquid feeds. The reactors were made of ⅜ inch (0.95 cm) 316 SS tubing, and were 12⅛ inches (30.8 cm) in length. The vaporizers were made of ⅜ inch (0.95 cm) 316 SS tubing and were 12⅜ inches (31.45 cm) in length. The reactors, vaporizers, and their respective effluent transfer lines were electrically heated (heat tape).

The reactor effluents were routed to chilled water condensers and knock-out pots. Condensed liquids were collected automatically, and then manually drained from the knock-out pots as needed. Non-condensed gases were passed through a manual back pressure regulator (BPR) and then scrubbed through water and vented to the fume hood. For each Example, 15 ml of catalyst (3 mm pellets) was loaded into reactor. Both inlet and outlet of the reactor were filled with glass beads (3 mm) to form the fixed bed. The following running conditions for catalyst screening were used: T=275° C., P=300 psig (2068 kPag), [Feed]=0.138 ml/min (pump rate), and [$H_2$]=513 sccm, gas-hourly space velocity (GHSV) =2246 $hr^{-1}$. The mixed feed comprised approximately 70 wt. % acetic acid and approximately 20 wt. % ethyl acetate. Other components included diethyl acetal, water, acetaldehyde and ethanol.

The crude product was analyzed by gas chromatograph (Agilent GC Model 6850), equipped with a flame ionization detector. Diethyl ether and ethyl acetate amounts are shown below in Table 3.

TABLE 3

ETHYL ACETATE AND DIETHYL ETHER PRODUCTION

|  | Ethyl Acetate (wt. %) | Diethyl Ether (wt. %) |
| --- | --- | --- |
| Example 2 | — | — |
| Example 3 | 27.32 | 0.14 |
| Example 4 | 36.18 | 0.04 |

As can be seen from Table 3, the catalyst of Examples 2-4 result in a low selectivity of the mixed feed to diethyl ether.

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for producing ethanol, comprising contacting a feedstock comprising hydrogen and acetic acid and/or ethyl acetate in a reactor at an elevated temperature in the presence of a catalyst, under conditions effective to form ethanol; wherein the catalyst comprises a precious metal and at least one active metal on a modified silica support, wherein the catalyst has at least 70% Lewis acid sites based on the total number of acid sites as measured by Fourier transform infrared spectroscopy of chemisorbed pyridine, and wherein the modified silica support comprises: (i) a support material; and (ii) a support modifier comprising a metal selected from the group consisting of tungsten, molybdenum, vanadium, niobium, and tantalum.

2. The process of claim 1, wherein the feedstock further comprises greater than 5 wt. % ethyl acetate.

3. The process of claim 1, wherein the feedstock further comprises ethyl acetate in an amount greater than 0 wt. %, wherein acetic acid conversion is greater than 20% and ethyl acetate conversion is greater than 5%.

4. The process of claim 1, wherein selectivity to diethyl ether is less than 1%.

5. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

6. The process of claim 1, wherein the catalyst has at least 80% Lewis acid sites, based on the total number of acid sites, as measured by Fourier transform infrared spectroscopy of chemisorbed pyridine.

7. The process of claim 1, wherein the modified silica support comprises cobalt tungstate.

8. The process of claim 1, wherein the precious metal is selected from the group consisting of rhodium, rhenium, ruthenium, platinum, palladium, osmium, iridium and gold.

9. The process of claim 1, wherein the at least one active metal is selected from the group consisting of copper, iron, vanadium, nickel, titanium, zinc, chromium, molybdenum, tungsten, tin, lanthanum, cerium, cobalt, manganese and combinations thereof.

10. The process of claim 1, wherein the catalyst is prepared by:
(a) impregnating a support material with a first solution to form a first impregnated support, wherein the first solution comprises a precursor to the support modifier metal selected from the group consisting of tungsten, molybdenum, niobium, vanadium, and tantalum;
(b) calcining the first impregnated support to form a modified silica support;
(c) impregnating the modified silica support with a second solution to form a second impregnated support, wherein the second solution comprises a precious metal precursor, and a precursor to at least one active metal; and
(d) calcining the second impregnated support to form the catalyst.

11. The process of claim 10, wherein the first solution further comprises a precursor to at least one active metal selected from the group consisting of copper, iron, vanadium, nickel, titanium, zinc, chromium, molybdenum, tungsten, tin, lanthanum, cerium, cobalt, manganese and combinations thereof.

12. The process of claim 11, wherein the precursor to at least one active metal in the first solution is the same precursor to at least one active metal in the second solution.

13. The process of claim 10, wherein the support material has no acidic acid sites prior to impregnating with the first solution.

14. A process for producing ethanol, comprising contacting a feedstock comprising hydrogen and acetic acid and/or ethyl acetate in a reactor at an elevated temperature in the presence of a catalyst, under conditions effective to form ethanol; wherein the catalyst comprises a modified silica support, and n metals, wherein n is from 2 to 6, and the metals are selected from the group consisting of rhodium, rhenium, ruthenium, platinum, palladium, osmium, iridium, copper, iron, vanadium, nickel, titanium, zinc, chromium, molybdenum, tungsten, vanadium, niobium, tantalum, tin, lanthanum, cerium, cobalt, manganese, and oxides thereof, wherein the hydrogenation catalyst has at least 70% Lewis acid sites, based on the percent of all acidic sites, as measured by Fourier transform infrared spectroscopy of chemisorbed pyridine.

15. The process of claim 14, wherein n is 3.

16. The process of claim 14, wherein the modified silica support comprises a silica support, a support modifier, and at least one active metal.

17. The process of claim 14, wherein the support modifier is selected from the group consisting of tungsten, molybdenum, niobium, vanadium, and tantalum.

18. The process of claim 14, wherein the at least one active metal are selected from the group consisting of copper, iron, vanadium, nickel, titanium, zinc, chromium, molybdenum, tungsten, tin, lanthanum, cerium, cobalt, manganese and combinations thereof.

19. The process of claim 14, wherein the catalyst is prepared by:
   (a) impregnating a support material with a first solution to form a first impregnated support, wherein the first solution comprises a precursor to a support modifier metal selected from the group consisting of tungsten, molybdenum, niobium, vanadium, and tantalum;
   (b) calcining the first impregnated support to form a modified silica support;
   (c) impregnating the modified silica support with a second solution to form a second impregnated support, wherein the second solution comprises a precursor to each of the at least one active metals; and
   (d) calcining the second impregnated support to form the catalyst.

* * * * *